US011249073B2

(12) United States Patent
Chiu et al.

(10) Patent No.: US 11,249,073 B2
(45) Date of Patent: Feb. 15, 2022

(54) METAL-CONTAINING SEMICONDUCTING POLYMER DOTS AND METHODS OF MAKING AND USING THE SAME

(71) Applicant: University of Washington through its Center for Commercialization, Seattle, WA (US)

(72) Inventors: Daniel T. Chiu, Seattle, WA (US); Wei Sun, Seattle, WA (US); Jiangbo Yu, Seattle, WA (US); Changfeng Wu, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 497 days.

(21) Appl. No.: 14/434,200

(22) PCT Filed: Oct. 8, 2013

(86) PCT No.: PCT/US2013/063917
§ 371 (c)(1),
(2) Date: Apr. 8, 2015

(87) PCT Pub. No.: WO2014/058903
PCT Pub. Date: Apr. 17, 2014

(65) Prior Publication Data
US 2015/0268229 A1    Sep. 24, 2015

Related U.S. Application Data (60) Provisional application No. 61/710,851, filed on Oct. 8, 2012.

(51) Int. Cl.
| | |
|---|---|
| *G01N 33/52* | (2006.01) |
| *C12N 5/09* | (2010.01) |
| *C09K 11/06* | (2006.01) |
| *C12N 13/00* | (2006.01) |

(52) U.S. Cl.
CPC .............. *G01N 33/52* (2013.01); *C09K 11/06* (2013.01); *C12N 5/0693* (2013.01); *C12N 13/00* (2013.01); *C09K 2211/1416* (2013.01); *C12N 2529/00* (2013.01); *G01N 2458/00* (2013.01)

(58) Field of Classification Search
CPC ............ G01N 2458/00; A61K 49/1827; A61K 49/1851
See application file for complete search history.

(56) References Cited

U.S. PATENT DOCUMENTS

| | | |
|---|---|---|
| 2004/0209376 A1 | 10/2004 | Natan et al. |
| 2011/0014473 A1 | 1/2011 | Ying et al. |
| 2011/0130616 A1 | 6/2011 | Seeney et al. |
| 2013/0164223 A1* | 6/2013 | Jeon ................. A61K 49/1839 424/9.322 |

FOREIGN PATENT DOCUMENTS

| | | |
|---|---|---|
| CN | 101148495 A | 3/2008 |
| CN | 101616950 A | 12/2009 |
| CN | 104903706 A | 9/2015 |
| EP | 2904381 A2 | 8/2015 |
| JP | 2016-506436 A | 2/2016 |
| WO | WO 2007/075495 A2 | 7/2007 |
| WO | WO 2011/057295 A2 | 5/2011 |
| WO | WO 2014/058903 A2 | 4/2014 |

OTHER PUBLICATIONS

Zhang et al., 2004 Polymer Microgels: Reactors for Semiconductor, Metal, and Magnetic Nanoparticles. JACS, 1.26: 7908-7914.*
Shen (2011. Biocompatible Polymer/Quantum Dots Hybrid Materials: Current Status and Future Developments. J. Functional Nanomaterials, vol. 2:355-372.*
Fratoddi et al. "Core shell hybrids based on noble metal nanoparticles and conjugated polymers: synthesis and characterization", Nanoscale Research Letters 2011, 6:98 (Year: 2011).*
Https://en.wikipedia.org/wiki/Iron_oxide printed online Apr. 16, 2021 (Year: 2021).*
Boyer et al. "The design and utility of polymer-stabilized iron-oxide nanoparticles for nanomedicine applications", NPG Asia Mater. 2(1) 23-30 (2010) (Year: 2010).*
Lanfester et al. "Semiconducting Polymer Nanospheres in Aqueous Dispersion Prepared by a Miniemulsion Process", Adv. Mater. 2002, 14, No. 9, May 3 (Year: 2002).*
Chan, et al. Hybrid semiconducting polymer dot-quantum dot with narrow-band emission, near-infrared fluorescence, and high brightness. J Am Chem Soc. May 2, 2012;134(17):7309-12. doi: 10.1021/ja3022973. Epub Apr. 23, 2012.
International search report and written opinion dated Apr. 9, 2014 for PCT/US2013/063917.
Extended European Search Report dated Mar. 2, 2016 for EP Application No. 13844736.2.
Geng, et al. Conjugated polymer and gold nanoparticle co-loaded PLGA nanocomposites with eccentric internal nanostructure for dual-modal targeted cellular imaging. Small. Aug. 2012; 8(15):2421-2419.
Howes, et al. Magnetic conjugated polymer nanoparticles as bimodal imaging agents. J Am Chem Soc. Jul. 21, 2010;132(28):9833-42. doi: 10.1021/ja1031634.
Jain, et al. Calculated absorption and scattering properties of gold nanoparticles of different size, shape, and composition: applications in biological imaging and biomedicine. Journal of Physical Chemistry B. Apr. 2006; 110(14):7238-7248.
Jin, et al. Near-infrared fluorescent dye-doped semiconducting polymer dots. ACS Nano. Feb. 22, 2011;5(2):1468-75. doi: 10.1021/nn103304m. Epub Jan. 31, 2011.

(Continued)

*Primary Examiner* — James W Rogers
(74) *Attorney, Agent, or Firm* — Christensen O'Connor Johnson Kindness PLLC (57) ABSTRACT

The present disclosure provides metal-containing (MC) semiconducting (SC) Pdots (MC-SC-Pdots) with beneficial functionalities in both cellular imaging and manipulation, among other applications. The Pdots comprise at least one nanoparticle comprising at least one metal, and a semiconducting polymer associated with the nanoparticle.

11 Claims, 6 Drawing Sheets

(56) References Cited

OTHER PUBLICATIONS

Li, et al. Conjugated Polymer Based Nanoparticles as Dual-Modal Probes for Targeted In Vivo Fluorescence and Magnetic Resonance Imaging. Advanced Functional Materials. Aug. 2012; 22(15):3107-3115.

Pecher, et al. Nanoparticles of conjugated polymers. Chem Rev. Oct. 13, 2010;110(10):6260-79. doi: 10.1021/cr100132y.

Sun, et al. A versatile method for generating semiconducting polymer dot nanocomposites. Nanoscale. Nov. 21, 2012;4(22):7246-9. doi: 10.1039/c2nr32055j.

Tian, et al. Amplified energy transfer in conjugated polymer nanoparticle tags and sensors. Nanoscale. Oct. 2010;2(10):1999-2011. doi: 10.1039/c0nr00322k. Epub Aug. 10, 2010.

Tuncel, et al. Conjugated polymer nanoparticles. Nanoscale. Apr. 2010;2(4):484-94. doi: 10.1039/b9nr00374f. Epub Mar. 6, 2010.

Wang, et al. Optical imaging of non-fluorescent nanoparticle probes in live cells. Analyst. Feb. 2010. 135(2):215-21. doi: 10.1039/b916395f Epub Dec. 17, 2009.

Wu, et al. Bioconjugation of ultrabright semiconducting polymer dots for specific cellular targeting. J Am Chem Soc. Nov. 3, 2010;132(43):15410-7. doi: 10.1021/ja107196s.

Wu, et al. Conjugated polymer dots for multiphoton fluorescence imaging. J Am Chem Soc. Oct. 31, 2007;129(43):12904-5. Epub Oct. 6, 2007.

Wu, et al. Design of highly emissive polymer dot bioconjugates for in vivo tumor targeting. Angew Chem Int Ed Engl. Apr. 4, 2011;50(15):3430-4. doi: 10.1002/anie.201007461. Epub Mar. 4, 2011.

Wu, et al. Energy Transfer in a Nanoscale Multichromophoric System: Fluorescent Dye-Doped Conjugated Polymer Nanoparticles. Phys Chem C Nanomater Interfaces. Feb. 14, 2008;112(6):1772-1781.

Wu, et al. Multicolor conjugated polymer dots for biological fluorescence imaging. ACS Nano. Nov. 25, 2008;2(11):2415-23. doi: 10.1021/nn800590n.

Wu, et al. Preparation and encapsulation of highly fluorescent conjugated polymer nanoparticles. Langmuir. Mar. 28, 2006;22(7):2956-60.

Wu, et al. Ratiometric single-nanoparticle oxygen sensors for biological imaging. Angew Chem Int Ed Engl. 2009;48(15):2741-5. doi: 10.1002/anie.200805894.

Wu, et al. Ultrabright and bioorthogonal labeling of cellular targets using semiconducting polymer dots and click cAngew Chem Int Ed Engl. Dec. 3, 2010;49(49):9436-40. doi: 10.1002/anie.201004260. hemistry.

Ye, et al. A compact and highly fluorescent orange-emitting polymer dot for specific subcellular imaging. Chem Commun (Camb). Feb. 7, 2012;48(12):1778-80. doi: 10.1039/c2cc16486h. Epub Jan. 4, 2012.

Ye, et al. Ratiometric temperature sensing with semiconducting polymer dots. J Am Chem Soc. Jun. 1, 2011;133(21):8146-9. doi: 10.1021/ja202945g. Epub May 11, 2011.

Office action dated Feb. 3, 2017 for EP Application No. 13844736.

Office action dated Sep. 27, 2016 for CN Application No. 201380052601.

Office action dated May 15, 2017 for CN Application No. 201380052601.0.

Office Action dated Sep. 18, 2017 for European Patent Application No. 13844736.2.

Office action dated Sep. 19, 2017 for JP Application No. 2015-535892.

Osaka. I., "Semiconducting polymers based on electron-deficient π-building units," Polymer Jounrla, 47:18-25, 2015.

Scaccabarozzi, A.D. and Stingelin, N., "Semiconducting:insulating polymer blends for optoelectronic applications—a review of recent advances," Journal of Materials Chemistry A, 2:10818-10824, 2014.

Tyutnev, A. et al., "Radiation-induced conductivity in polystyrene, a common insulating polymer with a hopping conduction," Journal of Applied Physics, 129:175107, 9 pages, published online May 5, 2021.

Chinese office action dated Jul. 31, 2018 for CN Application No. CN201380052601.

CN 201380052601.0 Third Office Action dated Feb. 5, 2018 (w/ English translation).

* cited by examiner

METAL-CONTAINING SEMICONDUCTING POLYMER DOTS AND METHODS OF MAKING AND USING THE SAME

CROSS REFERENCE TO RELATED APPLICATION

This application is a U.S. National Phase Application under 35 U.S.C. § 371 of International Application No. PCT/US2013/063917, filed Oct. 8, 2013, which claims the benefit of U.S. Provisional Patent Application No. 61/710,851, filed Oct. 8, 2012, the entire disclosure of which is incorporated by reference herein.

FIELD OF THE DISCLOSURE

The present disclosure provides semiconducting polymer dots (Pdots) including at least one metal, their methods of manufacture and methods of use.

BACKGROUND OF THE DISCLOSURE

Polymer dots (Pdots) have recently emerged as a new type of fluorescent nanoprobe that holds great promise in imaging applications. Compared to small fluorescent dyes and quantum dots (Qdots), Pdots possess high brightness, fast emission rates, and good photo-stability. The size of Pdots also can be modified without drastically affecting their emission spectra, increasing their utility across a broad range of applications.

SUMMARY OF THE DISCLOSURE

Pdot hybrids can provide additional functionalities that are not available to Pdots alone. For example, Pdot hybrids with quantum dots (Qdots) embedded in the Pdots (Pdot-Qdot) have been prepared by covalently linking semiconducting polymers functionalized with amine groups to the surface of Qdots. These Pdot hybrids show narrow-band and near-IR fluorescence emission with high brightness. Chan et al., J. Am. Chem. Soc., 2012, 134, 7309-7312.

Besides Qdots, many other inorganic nanoparticles (NPs) and particles exist and can be used to prepare Pdot-hybrids for a wide range of applications. The present disclosure utilizes metals to prepare metal-containing (MC) semiconducting (SC) Pdots (MC-SC-Pdots). As described more fully below, a variety of metals and polymers can be used to achieve beneficial effects associated with these hybrid MC-SC-Pdots. For example, gold (Au) particles or NPs comprising Au have been used as contrast agents for long-term observation and single-particle tracking in dark-field microscopy because Au does not photobleach. But in dark-field microscopy, it is difficult to distinguish Au from other intracellular micro- and nano-features that also strongly scatter light and thus give rise to signals similar to Au. This problem has been overcome by the current disclosure, which in particular embodiments, provides Au within the MC-SC-Pdots to provide Pdot hybrids with dual-modality imaging capability. In this way, Au-MC-SC-Pdots can be differentiated easily from other cellular features because only they can generate both strong dark-field and fluorescence signals. Here, fluorescence is used to help identify true Au-MC-SC-Pdot probes and dark-field is then used to carry out long-term imaging to take advantage of the optical stability of Au.

In another example, the metal is iron (Fe) or iron oxide ($FeO_x$). In these embodiments, the MC-SC-Pdots can be used in both bioimaging and sample preparation. For example, Fe or $FeO_x$-MC-SC-Pdots are attracted to and concentrated by a magnet; these hybrid $FeO_x$-MC-SC-Pdots emit strong fluorescence when excited by UV light. The $FeO_x$-MC-SC-Pdot-labeled cells can be manipulated and enriched using a permanent magnet. In some embodiments, the iron oxide containing Pdots can be used for multimodality imaging such as fluorescence imaging and magnetic resonance imaging.

Based in part on the foregoing, described herein are MC-SC-Pdots that are useful for a variety of applications including cellular labeling and manipulation (in vitro and in vivo).

DETAILED DESCRIPTION

Polymer dots (Pdots) have recently emerged as a new type of fluorescent nanoprobe that holds great promise in imaging applications. Pdot-based hybrids can provide additional functionalities that are not available to Pdots alone. The present disclosure provides metal-containing (MC) semiconducting (SC) Pdots (MC-SC-Pdots) with beneficial functionalities in both cellular imaging and manipulation, among other applications. In particular embodiments, the Pdots comprise at least one NP comprising at least one metal, and a polymer associated with the NP. In additional embodiments, the polymeric matrix can surround the NP. In additional particular embodiments, the NP comprises, consists of or consists essentially of one metal particle. In further embodiments, the NPs comprising at least one metal or consisting of one metal particle have a hydrophobic or hydrophilic polymer or other hydrophobic or hydrophilic molecule attached to the NP to form a "hydrophobic core" or a "hydrophilic core" to the MC-SC-Pdot. This hydrophobic core or hydrophilic core is then surrounded by the polymer matrix having a SC polymer therein. As used herein, "surrounded" includes complete encapsulation as well as 80% encapsulation, 85% encapsulation; 90% encapsulation, 95% encapsulation or 99% encapsulation.

Association between a NP, hydrophobic core or hydrophilic core and the polymer matrix can be association through a physical or chemical association. A physical association can arise from a range of forces, including but not limited to van de Waals, electrostatic, pi-stacking, hydrophobic, entropic forces and combinations thereof. A chemical association can be through a chemical bond.

Groups of the described MC-SC-Pdots can have varying average diameters depending on a particular application. In particular embodiments, the MC-SC-Pdots have an average diameter of 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm, 70 nm, 80 nm, 90 nm, 100 nm, 120 nm, 140 nm, 150 nm, 160 nm, 180 nm, or 200 nm, an average diameter of less than 100 nm, less than 80 nm, less than 60 nm, less than 40 nm, less than 30 nm, less than 20 nm, or less than 10 nm, an average diameter between 5 nm and 100 nm, between 20 nm and 100 nm, between 20 nm and 60 nm, between 20 nm and 40 nm, between 20 nm and 80 nm, between 40 nm and 80 nm, between 50 nm and 80 nm, between 60 nm and 80 nm, between 70 nm and 80 nm, between 10 nm and 40 nm, or any range bound by or between any of these listed values.

MC-SC-Pdots as disclosed herein can comprise a metal or a metal compound having at least one metal, metal alloy, metal salt and/or metal complex. The NP can comprise or consist essentially of a metal and other non-metal components or can consist essentially of or consist of a metal particle (metal(s) alone). The metal(s) can include, without limitation, Na, Li, Zn, Mg, Fe, Mn, Co, Ni, Cu, In, Si, Ga, Al, Pt, Pd, Ru, Rh, Re, Os, Ir, Ag, or Au. Further, oxides, complexes, and combinations of these metals can also be used in the described MC-SC-Pdots. In one embodiment, Au is used as a metal. In another embodiment, FeO$_x$ is used as a metal wherein x is equal to a/b and wherein a is 1, 2, 3, 4, 5, 6, 7, 8, 9, or 10 and b is 1, 2, 3, 4, 5, 6, 7, 8, 9, or 10.

A metal particle can be a single metal atom, a cluster of metal atoms, a lattice of metal atoms, a spacially distinct cluster or lattice of metal atoms, or a cluster or lattice (in particular embodiments, spacially distinct clusters or lattices) of metal compounds, alloys and/or oxides. A cluster of metal atoms can include 1, 2, 3, 4, 5, 6, 7, 8, 9, 10, 20, 30, 50, 100, 200, 500, 1,000, 10,000, 100,000, 1,000,000, 5,000,000, 10,000,000, 50,000,000, 100,000,000, 1,000,000,000, 5,000,000,000, 1,000,000,000,000, or more atoms. In some embodiments, only a single metal particle is included in a MC-SC-Pdot.

The NPs described herein can have an attached hydrophobic polymer, an attached hydrophilic polymer, or an attached amphiphilic polymer to form a hydrophobic core, a hydrophilic core or an amphiphilic core of the MC-SC-Pdots. These cores can aid in manufacture, deployment and/or use of the MC-SC-Pdots. In particular embodiments, hydrophobic polymers for attachment can include, without limitation, poly(meth)acrylate, polyacrylamide, polyisobutylene, polydiene, polyphenylene, polyethylene, polylactide, polystyrene, polysiloxane, poly(vinylpyrrolidone), polyurethane, a block copolymer thereof, a random or alternating copolymer thereof, and the like. In particular embodiments, hydrophilic polymers for attachment can include, without limitation, poly(ethylene glycol), poly(vinyl pyridine), polyalkylene glycol, poly(ethylene oxide), polypropylene glycol, polyoxyalkylene, starch, poly-carbohydrate, polysialic acid, and the like. In one embodiment, the hydrophilic polymer is polyalkylene glycol. In a more specific embodiment, the hydrophilic is polyethylene glycol (PEG).

The MC-SC-Pdots generated using the methods described herein include a high percentage or content of SC polymer or a blend of semiconducting polymer and other polymer(s) to form the polymer matrix that surrounds the metal-containing NP, hydrophobic core, hydrophilic core or amphiphilic core. The high percentage of SC polymer can be important in biomedical applications that demand high fluorescence brightness from the MC-SC-Pdots described, because a higher percentage of SC polymers translate into brighter MC-SC-Pdots.

For example, of all the polymers present in the MC-SC-Pdots, the percentage of SC polymer present can be higher than 10%, higher than 30%, higher than 50%, higher than 80%, higher than 90%, higher than 95%, or higher than 99% v/v of the MC-SC-Pdots. In particular embodiments, the SC polymer can account for 40% 50%, 60%, 70%, 80%, 90%, 95%, or 99% v/v, at least 50%, at least 60%, at least 70%, at least 80%, at least 90%, at least 95% v/v or at least 99% v/v or between 50% and 80%, between 40% and 90%, or between 60% and 80% v/v of the MC-SC-Pdots. In another embodiment, the SC polymer matrix can account for 50%, 60%, 70%, 80%, 90%, 95%, or 99% v/v, at least 50%, at least 60%, at least 70%, at least 80%, at least 90%, at least 95% or at least 99% v/v, between 50% and 80%, between 50% and 90%, or between 60% and 80% v/v of the MC-SC-Pdots. V/v percentages of the SC polymer or SC polymer matrix can also include any range bound by or between any of these listed values. Volume ratio or percentage (v/v) can be verified based on TEM imaging or based on a dynamic light scattering measurement to obtain the average diameter of the metal NP versus the MC-SC-Pdot.

The SC polymer or polymeric blend of SC polymers and non-SC polymers associated with the Pdot can be tailored to suit a particular application and can be made to be hydrophobic, hydrophilic or amphiphilic. Semiconducting polymers can have a characteristic brightness that stems from a number of favorable characteristics, including their large absorption cross-sections, fast emission rates, and high fluorescence quantum yields. Semiconducting polymers include polymers comprising units of structures with delocalized pi-electrons.

Suitable SC polymers used to form the polymeric matrix can include SC homopolymers including without limitation, fluorene polymers, phenylene vinylene polymers, phenylene polymers, phenylene ethynylene polymers, benzothiazole polymers, thiophen polymers, carbazole fluorene polymers, fluorone polymers, perylene polymers, rhodamine polymers, cyanine polymers, squaraine polymers, porphyrin polymers, phthalocyanine polymers, coumarin polymers, xanthene polymers, boron-dipyrromethene-based polymers, metal-complex based polymers, and derivatives thereof. Combinations or heteropolymers of the above listed polymers can also be used.

More particular exemplary SC polymers appropriate for use with the MC-SC-Pdots disclosed herein are listed in Table 1 below.

TABLE 1

Non-limiting examples of SC polymers

Fluorene Polymers: Poly(9,9-dihexylfluorenyl-2,7-diyl) (PDHF); Poly(9,9-dioctylfluorenyl-2,7-diyl) (PFO)
Fluorene-Based Copolymers: Poly[{9,9-dioctyl-2,7-divinylene-fluorenylene}-alt-co-{2-methoxy-5-(2-ethylhexyloxy)-1,4-phenylene}] (PFPV); Poly[(9,9-dioctylfluorenyl-2,7-diyl)-co-(1,4-benzo-{2,1,3}-thiadiazole)] (PFBT); Poly[(9,9-dioctylfluorenyl-2,7-diyl)-co-(4,7-Di-2-thienyl-2,1,3-benzothiadiazole)] (PFTBT); Poly[(9,9-dioctylfluorenyl-2,7-diyl)$_{0.9}$-co-(4,7-Di-2-thienyl-2,1,3-benzothiadiazole)$_{0.1}$] (PF-0.1TBT)
Phenylene Vinylene Polymers: Poly[2-methoxy-5-(2-ethylhexyloxy)-1,4-phenylenevinylene] (MEH-PPV);
Phenylene Ethynylene Polymers: Poly(2,5-di(3',7'-dimethyloctyl)phenylene-1,4-ethynylene (PPE)
Boron Dipyrromethene (BODIPY)-based Copolymers: Poly[(BODIPY)$_{0.02}$-fluorene], Poly[(BODIPY)$_{0.05}$-fluorene], Poly[(BODIPY)$_{0.10}$-fluorene], Poly[(BODIPY)$_{0.25}$-fluorene], Poly[(BODIPY)$_{0.50}$-fluorene]

In particular embodiments, the SC polymer is a copolymer comprising at least two different SC units. For example, a SC copolymer may contain both fluorene and benzothiazole SC units present at a given ratio. Typical SC units used to synthesize SC copolymers include, but are not limited to fluorene units, phenylene vinylene units, phenylene units, phenylene ethynylene units, benzothiazole units, thiophen units, carbazole fluorene units, boron-dipyrromethene units, and derivatives thereof. The different SC units may be segregated, as in a block copolymer, or intermingled. As used herein, a SC copolymer is represented by writing the identity of the major SC species. For example, PFBT is a SC polymer containing fluorene and benzothiazole units at a certain ratio. In some cases, a dash is used to indicate the percentage of the minor SC species and then the identity of the minor SC species. For example, PF-0.1BT is a SC copolymer containing 90% PF and 10% BT. In another embodiment, the SC polymer is a copolymer comprising at least three, four, five, six, seven, or more different SC units.

In other embodiments, a blend of SC polymers can be used. The blends may include any combination of SC homopolymers, copolymers, and oligomers. Semiconducting polymer blends used to form MC-SC-Pdots may be selected in order to tune the properties of the resulting MC-SC-Pdots, for example, to achieve a desired excitation or emission spectra for the MC-SC-Pdot.

The MC-SC-Pdots described herein can have characteristic absorption spectra including one or more absorption peaks. In one embodiment, the Pdots can have a peak of absorption at 350 nm, 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 520 nm, 525 nm, 530 nm, 540 nm, 550 nm, 560 nm, 570 nm, 580 nm, 590 nm, 600 nm, 610 nm, 620 nm, 630 nm, 640 nm, 650 nm, 660 nm, 670 nm, 680 nm, 690 nm, 700 nm, 720 nm, 740 nm, 750 nm, 760 nm, 770 nm, 780 nm, 790 nm, 800 nm, 810 nm, 820 nm, 830 nm, 840 nm, 850 nm, 860 nm, between 520 nm and 530 nm, between 400 nm and 640 nm, between 650 nm and 850 nm, between 350 nm and 600 nm, between 350 nm and 850 nm, or between 400 nm and 600 nm. In other embodiments, absorptions can be at 405 nm, 488 nm, 532 nm, 560 nm, 633 nm, and between 650 nm and 850 nm and can also include any range bound by or between any of these listed values.

The Pdots can also fluoresce when supplied with energy. Fluorescence can occur at wavelengths in the visible region from 400 nm to 700 nm. Fluorescence can occur at wavelengths in the near ultraviolet region from 300 nm to 400 nm. Fluorescence can also occur at wavelengths in the near-infrared or infrared region of the electromagnetic spectrum. Near-infrared emission refers to electromagnetic radiation having a wavelength between 700 nm and 1500 nm.

Methods of MC-SC-Pdot Formation

To prepare MC-SC-Pdots, two main approaches are described. One is based on miniemulsion and the second is based on nanoprecipitation.

1. Miniemulsion Formation Method. Amphiphilic surfactant molecules can be used to form water-miscible micelles that contain hydrophobic SC polymers. MC-SC-Pdots formed according to this mini-emulsion method, however, contain a fairly small percentage of fluorescent SC polymers (1.2%-8% of the polymer matrix) and they can also be quite large, ranging in average diameters or size from 120 nm to 180 nm or larger.

2. Nanoprecipitation Formation Method. Smaller MC-SC-Pdots than those produced by mini-emulsion can be more desirable because they can possess better cellular labeling and biodistribution properties. In comparison to the miniemulsion method, Pdots prepared by nanoprecipitation can be smaller and can be easily conjugated to biomolecules, such as streptavidin, by covalent bonding. Additionally, with nanoprecipitation methods, the number of embedded NPs can be reduced to a single one, for example, a NP comprising, consisting essentially of or consisting of a single metal particle.

In an exemplary nanoprecipitation process, hydrophobic, phase-transferred metal-containing NPs are mixed with at least one SC polymer in an aqueous solution to form MC-SC-Pdots.

The phase-transferred NPs can be formed by contacting NPs with a hydrophobic solvent. That is, in order to transfer NPs from an aqueous environment into a hydrophobic solvent, the NPs can be or can be made hydrophobic in nature, for example, have a hydrophobic coating or be formed of a hydrophobic polymer or molecule. In one embodiment, the NPs can be reacted with a hydrophobic, reactive compound to coat the surface of the NP in order to partition it into the hydrophobic solvent. Such a hydrophobic, reactive compound can be a SC polymer with thiol-terminated functional groups. Such a polymer can be, without limitation, thiol-terminated polystyrene, thiol-terminated poly(vinylpyrrolidone), thiol-terminated poly(4-vinyl pyridine) or thiol-terminated poly(butadiene).

Once the surface of NPs is rendered hydrophobic, they can be dispersed homogeneously in hydrophobic solvents. Appropriate hydrophobic solvents include, without limitation, ether, toluene, tetrahydrofuran (THF), methane, butane, propane, pentane, hexane, and the like. In one embodiment, the solvent can be toluene.

Once phase transferred, the NPs can be mixed with the SC polymer in the aqueous environment. Such mixing can be accomplished using a physical means such as a stir bar, a vortex, sonication or the like. In one embodiment, the mixing is by sonication.

In order to properly form MC-SC-Pdots, the concentration of the SC polymer can be provided at a concentration greater than that of NPs. The ratio of SC polymer to NPs can be, without limitation, 1.5:1, 2:1, 2.5:1, 3:1, 3.5:1, 4:1, 5:1, 6:1, 7:1, 8:1, 9:1, 10:1, greater than 1:1, greater than 2:1, greater than 3:1, greater than 4:1, or greater than 5:1.

Under certain conditions, the formation of MC-SC-Pdots can be accompanied by the formation of empty Pdots, or Pdots not containing at least one NP. Desired MC-SC-Pdots comprising at least one NP can be separated from empty Pdots using a step gradient such as a sucrose step gradient or any other appropriate step gradient. Desired MC-SC-Pdots can also be separated from empty Pdots using centrifugation. In some embodiments, both a step gradient step and a centrifugation step can be utilized to separate MC-SC-Pdots from empty Pdots.

Figure 1:
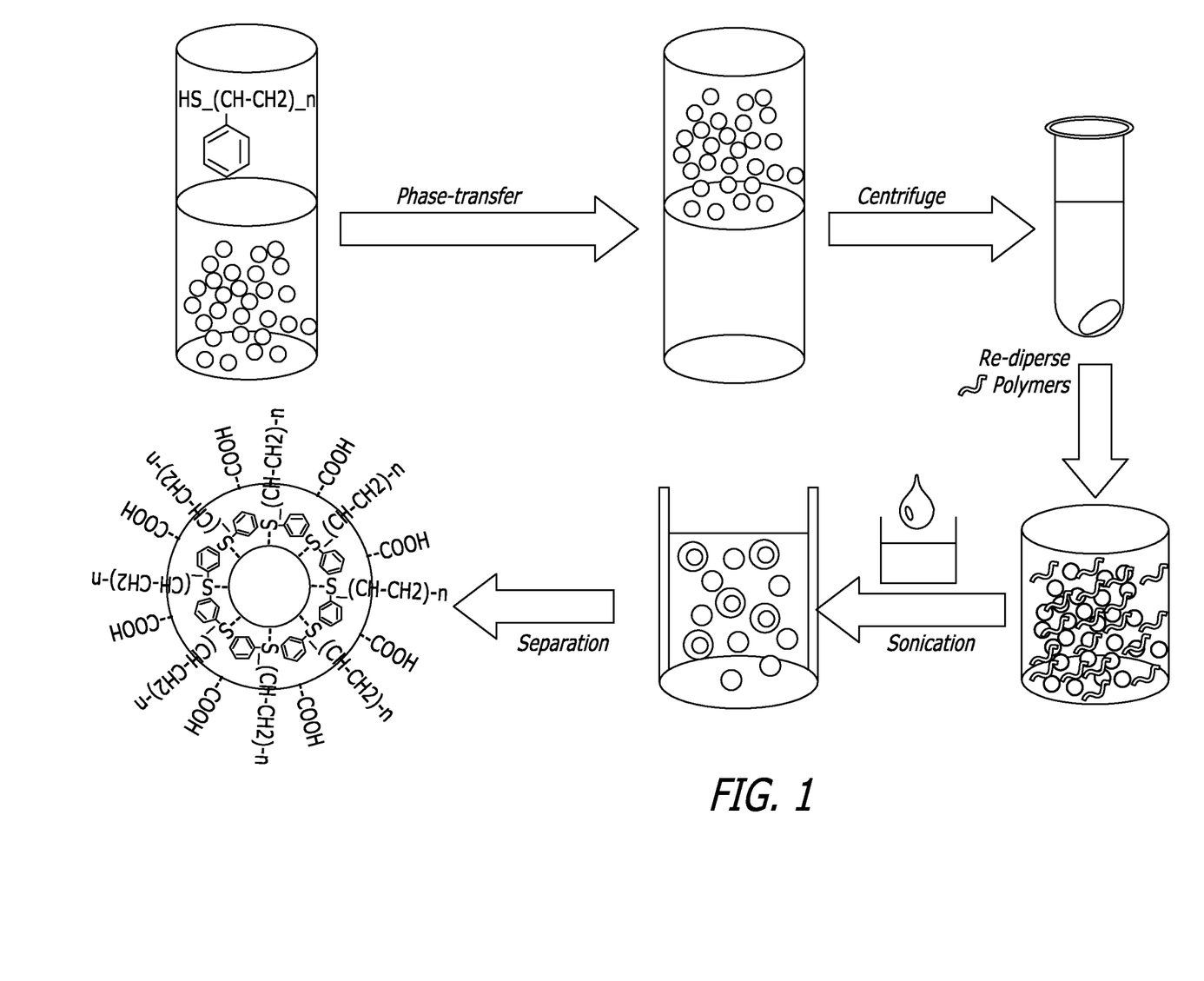
FIG. 1 illustrates a procedure for generating MC-SC-Pdots as described herein, which have a single gold (Au) particle embedded in each Pdot (Au-MC-SC-Pdot).

Formation & Description of Au-MC-SC-Pdots and $FeO_x$-MC-SC-Pdots. The formation of Au-MC-SC-Pdots and $FeO_x$-MC-SC-Pdots are provided as more particular examples of the methods described above. Generally, Au-NPs are first synthesized in aqueous solution, and then modified to become hydrophobic on the surface via phase-transfer into toluene, assisted by thiol-terminated polystyrene. After phase-transfer, the upper toluene solution is centrifuged to collect hydrophobic Au-NPs. NP pellets are re-dispersed in THF together with the hydrophobic SC polymer. This THF solution is then injected into pure water under sonication to produce Au-MC-SC-Pdots (FIG. 1).

In other embodiments, $FeO_x$—NPs can be purchased which already include a hydrophobic surface and are well dispersed in toluene. Therefore, these NPs can be directly centrifuged and re-dispersed in THF with the SC polymers.

Figure 2A:
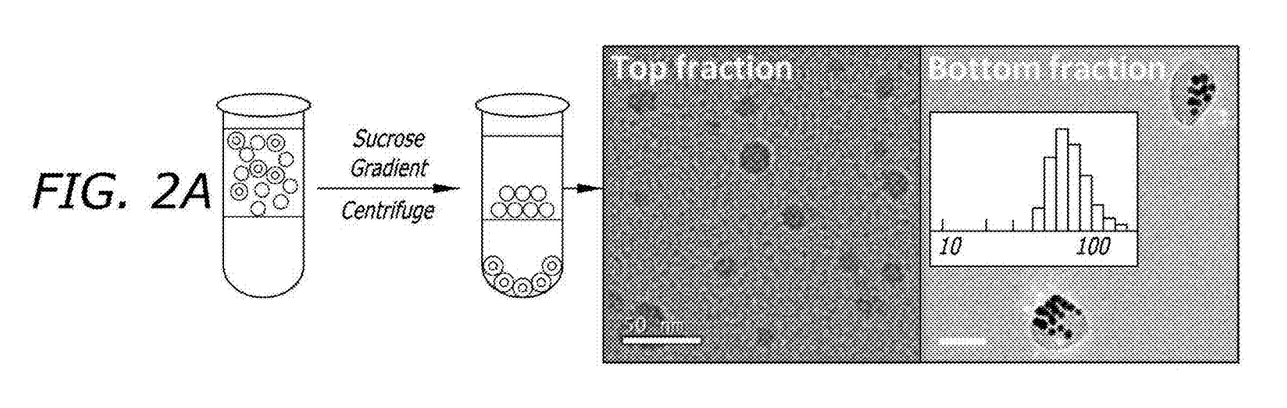
FIGS. 2A-C illustrate separation of Pdots containing Au or FeOx from empty Pdots. (A) Schematic depicting the purification procedure using centrifugation with a step sucrose gradient. Transmission electron microscopy (TEM) images of empty Pdots retrieved from the fraction above the sucrose solution (left) and Au-MC-SC-Pdots from the bottom fraction of the tube (right). The inset histogram shows the size distribution of Au-MC-SC-Pdots. The average diameter was 64 nm. (B) TEM image of MC-SC-Pdots containing a single Au particle and a histogram showing the number of Au particles in each MC-SC-Pdot. The average size was 28 nm. The inset histogram is the size distribution of Au-MC-SC-Pdots. (C) TEM image of $FeO_x$-MC-SC-Pdots. The average size was 52 nm. The used $FeO_x$ particles embedded inside the hybrid Pdots were 40 nm in average diameter. The inset histogram is the size distribution of $FeO_x$-MC-SC-Pdots. Scale bar represents 50 nm.

To help ensure that all Au and/or $FeO_x$—NPs present in solution are encapsulated within Pdots, SC polymer concentration in solution is generally kept higher than that of the NPs. Because Au-MC-SC-Pdots and $FeO_x$-MC-SC-Pdots have a much higher density than the empty Pdots they can be separated from the empty Pdots. FIG. 2A illustrates the purification procedure in which a sucrose step gradient is used. The heavier MC-SC-Pdots penetrate the sucrose layer and settle to the bottom of the centrifuge tube, while the lighter empty Pdots remain above the sucrose layer.

FIG. 2A also illustrates transmission electron microscopy (TEM) images of Pdots retrieved from a solution above the sucrose layer and those at the bottom of the centrifuge tube. In the TEM images, no empty Pdots were seen in the pellet, or any Au-MC-SC-Pdots in the top fraction. This result indicates successful purification of Au-MC-SC-Pdots from empty Pdots with nearly 100% yield. In other embodiments, yields of greater than 80%, greater than 85%, greater than 90%, greater than 95%, greater than 96%, greater than 97%, greater than 98%, or greater than 99% can be acceptable. In one embodiment, a high concentration of Au-NPs is used, which results in large Pdots (64 nm in diameter) that contained multiple Au-NPs.

Figure 2B:
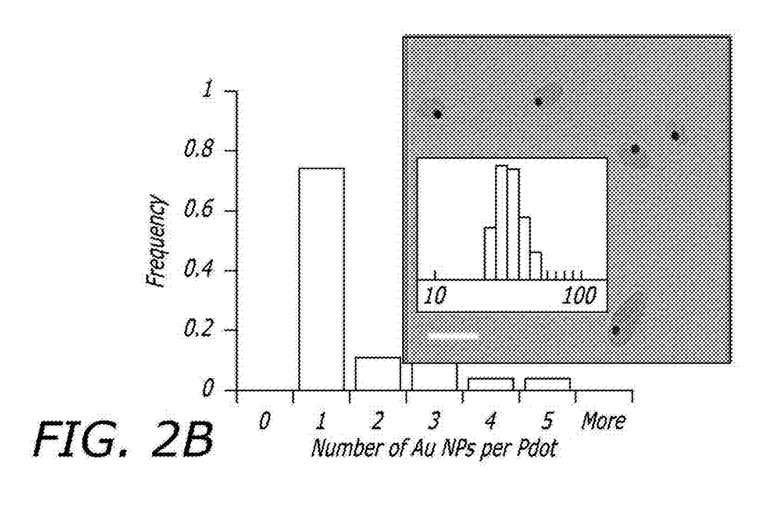
Figure 2C:
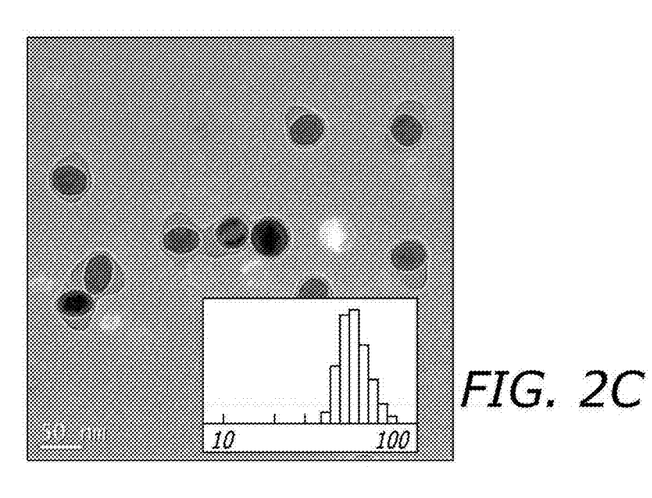

The size of the Au-MC-SC-Pdots can be further reduced when the number of embedded Au-NPs is decreased. For example, when the concentration of initially added Au-NPs is sufficiently low, the occupancy of Au-NPs per Pdot decreases. Pdots containing only a single Au—NP were generated (see FIG. 2B). The average size of singly occupied Au-MC-SC-Pdots was measured to be 28 nm. Other average sizes can be achieved as described herein. This strategy for generating Pdots with single encapsulated NPs can also work for $FeO_x$-MC-SC-Pdots (see FIG. 2C).

Figure 3A:
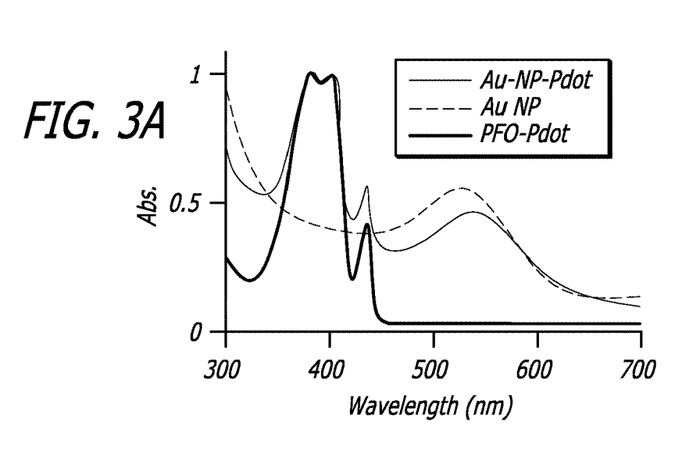
FIGS. 3A-D illustrate optical characterization of MC-SC-Pdots prepared as described herein. The (A) absorption (Abs.) and (B) emission (Flu.) spectra of Au-MC-SC-Pdots. The excitation wavelength was 380 nm, and the SC polymer was poly(9,9-dioctylfluorenyl-2,7-diyl) (PFO). The (B) absorption and (D) emission spectra of $FeO_x$-MC-SC-Pdots. The excitation wavelength was 457 nm, and the SC polymer was Poly[(9,9-dioctylfluorenyl-2,7-diyl)-co-(1,4-benzo-{2,1,3}-thiadiazole)] (PFBT).
Figure 3B:
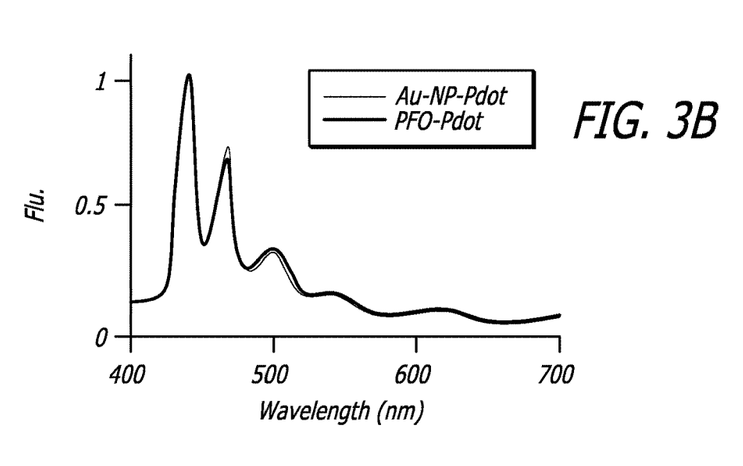
Figure 3C:
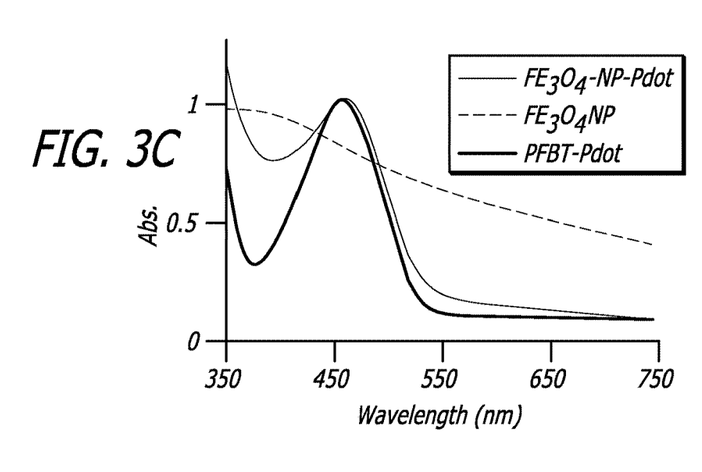
Figure 3D:
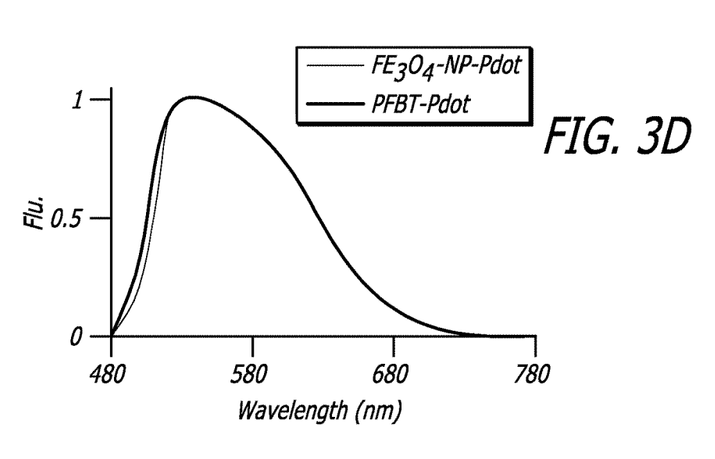

Optical properties of the Au-MC-SC-Pdot and $FeO_x$-MC-SC-Pdot hybrids can also be characterized. Au-MC-SC-Pdots have a new peak at 525 nm in the absorption spectrum that was distinct from a peak obtained from pure PFO Pdots (FIG. 3A). This new peak is from the characteristic Localized Surface Plasmon Resonance (LSPR) of Au-NPs. Compared to bare Au-NPs dispersed in water, the LSPR peak of Au-MC-SC-Pdots is slightly red-shifted. This red shift is believed to be caused by the close proximity between Au-MC-SC-Pdots and the change in the local environment around the Au-MC-SC-Pdots because the Pdot has a higher refractive index than water. The emission spectra of Au-MC-SC-Pdots and pure PFO Pdots are also similar. As illustrated in FIG. 3B, the absorption peak for $FeO_x$-MC-SC-Pdots is a little broadened because of the wide band absorption of $FeO_x$—NPs; the shape of fluorescence emission spectrum of the SC polymer is not affected by the $FeO_x$—NPs.

The NP within the MC-SC-Pdot has the potential to quench the MC-SC-Pdot's fluorescence. To determine the extent of this potential issue, the quantum yield (QY) values of the various MC-SC-Pdots can be measured. The QY value for pure PFO Pdots is 37%; for Au-MC-SC-Pdots with multiple Au-NPs, it is 7%. When the number of Au-NPs per MC-SC-Pdot is decreased to 1, the QY of MC-SC-Pdot is increased to 18%. Given the fact that each MC-SC-Pdot can be 30 times brighter than a Qdot, this 2 to 5 fold decrease in QY is manageable. It should also be noted that the fluorophore density of the MC-SC-Pdots prepared as described herein is significantly higher than that of MC-SC-Pdots prepared by miniemulsion methods. For example, the MC-SC-Pdots described herein, 90% (10 parts SC polymer, 1 part PS-PEG-COOH) of the polymer matrix is fluorescent SC polymer. Therefore, the MC-SC-Pdots prepared using the described nanoprecipitation methods retain much of their desirable optical characteristics.

Methods described can be generalizable for the formation of other MC-SC-Pdots for creating other multi-functional MC-SC-Pdot probes. In one embodiment, these methods can generate MC-SC-Pdots with a composition that includes a high percentage or content of fluorescent SC polymers, which in turn results in highly bright MC-SC-Pdots.

Exemplary MC-SC-Pdot Applications and Associated Considerations.

The MC-SC-Pdots described herein can be useful in many different diagnostic scenarios and/or therapeutic procedures. In one example, Au-MC-SC-Pdots can be used in dual-modality imaging in which co-localization of fluorescence from Au-MC-SC-Pdots and scattering from Au was used to identify Au-MC-SC-Pdot probes for downstream single-particle tracking and cellular imaging.

In other embodiments, methods for manipulating target cells using magnetism are disclosed. In these embodiments, a magnetic NP is embedded within the MC-SC-Pdot and the Pdot is associated with target cells. Application of a magnetic field can manipulate the target cells. Manipulation can include, without limitation, attraction, isolation, repulsion, localization, purification, transferring, or the like. In particular embodiments, the magnetic NP can include Fe, Ni, Co, Ga, oxides thereof, complexes thereof, combinations thereof, and combinations and complexes with non-magnetic metals. In one embodiment, the metal particle is $FeO_x$ wherein x is equal to a/b and wherein a is 1, 2, 3, 4, 5, 6, 7, 8, 9, or 10 and b is 1, 2, 3, 4, 5, 6, 7, 8, 9, or 10.

In order to render the Pdots able to attach to a target cell or other substance, the Pdot can first be coated with an appropriate polymer or can include an appropriate polymer matrix. An appropriate polymer coating or polymer matrix can include polymers with end groups susceptible to reactions with target molecules. In one embodiment, a polymer used to form a polymer matrix can include carboxylic acid terminated polymers such as polystyrene-poly(ethylene glycol).

Once the Pdot has an active surface such as by having free carboxylic acid groups, a biologically active target molecule can be attached. The biologically active compound can be tailored for a specific target cell, cell line, or substance. For example, the biologically active compound can be streptavidin which can target and attach to cancer cells.

Once attached to a target cell, cell line or substance, a magnetic field can be applied to move or otherwise manipulate the target cell, cell line, or substance to a location remote from its origin where, in particular examples, it can be separated or otherwise removed from the body or other vesicle.

For $FeO_x$-MC-SC-Pdots in particular, $FeO_x$-MC-SC-Pdots containing magnetic NPs of various sizes were prepared. During $FeO_x$-MC-SC-Pdots preparation, the high molecular weight polymer PS-PEG-COOH was blended into the hybrid Pdots. The carboxylic acid groups on the MC-SC-Pdots' surface enabled facile bioconjugation with streptavidin. The target cell line was then conjugated with bioconjugated $FeO_x$-MC-SC-Pdots thereby labeling the cells. The labeled cells were then attracted to a magnet. Accordingly, in embodiments disclosed herein, $FeO_x$-MC-SC-Pdots were employed in sample preparation, where cells tagged with $FeO_x$-MC-SC-Pdots were isolated using an external magnet. The cells were also detected and imaged based on the intense fluorescence of the $FeO_x$-MC-SC-Pdots.

Given that stronger magnet and magnetic NPs can be developed based on the present methods, the cell separation efficiency may be further improved.

Exemplary Embodiments

1. A metal-containing (MC) semiconducting (SC) polymer dot (Pdot) comprising, consisting essentially of or consisting of:
   (i) a nanoparticle (NP) comprising metal and
   (ii) A SC Polymer Associated with the NP,
   wherein the SC polymer comprises at least 50% v/v of the MC-SC-Pdot or wherein a group of the MC-SC-Pdots has an average diameter of less than 80 nm.
2. The MC-SC-Pdot of embodiment 1, wherein the NP consists essentially of or consists of one metal particle.
3. The MC-SC-Pdot of embodiment 1 or 2, wherein the metal or one metal particle comprises, consists essentially of or consists of Na, Li, Zn, Mg, Fe, Mn, Co, Ni, Cu, In, Si, Ga, Al, Pt, Pd, Ru, Rh, Re, Os, Ir, Ag, Au, an oxide thereof, a complex thereof, an alloy thereof, or a combination thereof.
4. The MC-SC-Pdot of embodiment 1, 2 or 3, wherein the metal or one metal particle comprises, consists essentially of or consists of Au or Fe.
5. The MC-SC-Pdot of embodiment 1, 2 or 3, wherein the metal or one metal particle comprises, consists essentially of or consists of $FeO_x$ wherein x is equal to a/b and wherein a is 1, 2, 3, 4, 5, 6, 7, 8, 9, or 10 and b is 1, 2, 3, 4, 5, 6, 7, 8, 9, or 10.
6. The MC-SC-Pdot of embodiment 1, 2, 3, 4, or 5 wherein the SC polymer forms at least 50% v/v of the MC-SC-Pdot and wherein a group of the MC-SC-Pdots has an average diameter of less than 80 nm.
7. The MC-SC-Pdot of embodiment 1, 2, 3, 4, 5 or 6 wherein the SC polymer forms at least 80% or at least 90% v/v of the MC-SC-Pdot.
8. The MC-SC-Pdot of embodiment 1, 2, 3, 4, 5, 6 or 7 wherein the NP is attached to a hydrophobic polymer to form a hydrophobic core.
9. The MC-SC-Pdot of embodiment 1, 2, 3, 4, 5, 6, 7 or 8 having an absorption wavelength between 350 nm and 850 nm.
10. A process of nanoprecipitating MC-SC-Pdots of embodiment 1, 2, 3, 4, 5, 6, 7, 8 or 9 comprising, consisting essentially of or consisting of:
    mixing hydrophobic, phase-transferred NPs comprising a metal with a SC polymer in an aqueous solution thereby trapping the NPs within a matrix of the SC polymer and thereby forming MC-SC-Pdots.
11. The process of embodiment 10, wherein the NP consists essentially of or consists of one metal particle.
12. The process of embodiment 10 or 11, wherein the MC-SC-Pdots are separated from empty Pdots using a sucrose step gradient.
13. The process of embodiment 12, wherein the MC-SC-Pdot are further separated from empty Pdots using centrifugation.
14. The process of embodiment 10, 11, 12 or 13 wherein each MC-SC-Pdot comprises, consists essentially of or consists of one NP.
15. The process of embodiment 10, 11, 12 or 13, further comprising contacting NPs with toluene to form the hydrophobic, phase-transferred NPs.
16. The process of embodiment 15, wherein the toluene includes semiconducting polymers with thiol-terminated functional groups.
17. The process of embodiment 15 or 16, further comprising, consisting essentially of or consisting of separating the hydrophobic, phase-transferred NPs from the toluene using centrifugation.
18. The process of embodiment 10, 11, 12, 13, 14, 15, or 16 wherein the mixing is performed with sonication.
19. The process of embodiment 10, 11, 12, 13, 14, 15, 16 or 17 wherein the SC polymer is at a higher concentration than the hydrophobic, phase-transferred NPs during the mixing.
20. A method of manipulating target cells using magnetism by associating a MC-SC-Pdot of embodiment 1, 2, 3, 4, 5, 6, 7, 8 or 9 with target cells and applying a magnetic field in an area of the target cells thereby manipulating the target cells.
21. The method of embodiment 20, wherein the MC-SC-Pdot NP consists essentially of or consists of one metal particle.
22. The method of embodiment 20 or 21, wherein the metal or one metal particle comprises, consists essentially of or consists of Fe, Ni, Co, Ga, oxides thereof, complexes thereof, alloys thereof, combinations thereof, and combinations and complexes with non-magnetic metals.

23. The method of embodiment 20, 21 or 22, wherein the metal or one metal particle comprises, consists essentially of or consists of Fe or an oxide thereof.
24. The method of embodiment 20, 21 or 22, wherein the one metal particle comprises, consists essentially of or consists of $FeO_x$ wherein x is equal to a/b and wherein a is 1, 2, 3, 4, 5, 6, 7, 8, 9, or 10 and b is 1, 2, 3, 4, 5, 6, 7, 8, 9, or 10.
25. The method of embodiment 20, 21, 22, 23 or 24 wherein the SC polymer comprises carboxylic acid terminated polystyrene-poly(ethylene glycol) polymers.
26. The method of embodiment 25, wherein the carboxylic acid groups on the carboxylic acid terminated polystyrene-poly(ethylene glycol) polymers bioconjugate with a biologically active compound.
27. The method of embodiment 20, 21, 22, 23, 24, 25 or 26, wherein the biologically active compound is streptavidin.
28. The method of embodiment 27, wherein the target cells are cancer cells.

Examples

1. Materials. Poly(9,9-dioctylfluorenyl-2,7-diyl) end capped with dimethyl phenyl (PFO, MW 120000 Da), and poly[(9,9-dioctylfluorenyl-2,7-diyl)-co-(1,4-benzo-(2,10, 3)-thiadiazole)] (PFBT, MW 157000 Da) were purchased from American Dye Source Inc. (Quebec, Canada). Thiol-terminated polystyrene (PSSH, MW 1000 Da) was purchased from Polymer Source Inc. (Quebec, Canada). Tetrachloroauric acid ($HAuCl_4$), sodium borohydride ($NaBH_4$), potassium carbonate ($K_2CO_3$), 1-Ethyl-3-[3-dimethylaminopropyl]carbodiimide hydrochloride (EDC), and magnetic NPs (10 nm, 20 nm average size, 5 mg/mL in toluene) were obtained from Sigma (St. Louis, Mo.). Magnetic NPs (40 nm average size, oleic acid coating, 25 mg/mL in chloroform) were purchased from Ocean NanoTech (Springdale, Ark.). Polystyrene-grafted ethylene oxide functionalized with carboxyl groups (PS-PEG-COOH; MW 21,700 Da of PS moiety; 1200 Da of PEG-COOH; polydispersity, 1.25) was from Polymer Source Inc. (Quebec, Canada). Sucrose was ordered from Avantor Performance Materials (Phillipsburg, N.J.).
2. Synthesis of Au—NPs. To 100 mL MilliQ water in an ice bath was charged 4 mL of 1.0% tetrachlorauric acid ($HAuCl_4$) aqueous solution and 1.3 mL of 0.2 M $K_2CO_3$. The solution was vigorously stirred, after which 1.0 mL of 1.54 mg/mL sodium borohydride solution (kept in ice bath) was added. This procedure was repeated 5 times (5 mL in total). The solution was then stirred overnight at 4° C.
3. Preparation of Au-MC-SC-Pdots. To 4-mL toluene containing 1 mg/mL PSSH was charged 2 mL of the Au NPs solution and mixed. After being vigorously shaken, the mixture was placed on the bench and allowed to phase-separate. After the Au NPs were phase-transferred to the upper toluene solution, the bottom water solution was discarded. Anhydrous sodium sulfate was added to dry the toluene. Then the Au NPs containing toluene solution were centrifuged at 14,000 rpm for 40 min. The pellet was re-dispersed in 2 mL tetrahydrofuran (THF). 500 μL of 1 mg/mL PFO and 50 μL of 1 mg/mL PS-PEG-COOH solution were added to the THF solution containing Au NPs. An additional amount of THF was added to adjust the final volume to 5 mL. The 5-mL mixture was then quickly injected into 10 mL of MilliQ water under vigorous sonication. The THF was removed by blowing nitrogen gas into the solution at 90° C. The THF-free Pdot solution was subsequently sonicated for 1-2 minutes and filtrated through a 0.2-μm cellulose membrane filter.
4. Purification of Au-MC-SC-Pdots. To a centrifuge tube was charged 1.5 mL of 1.5 M sucrose-water solution, after which 2 mL of the Au-MC-SC-Pdot solution as prepared above was placed on top of the sucrose layer. The centrifuge tube was put into a Beckman Optima™ Max-E Ultracentrifuge machine and spun at 45000 rpm for 45 min. The solution above the sucrose layer was collected and labeled as "pure Pdots". The pellet that formed at the bottom of the sucrose layer was re-dispersed in 2 mL of water with sonication and was labeled as "Au—NP-Pdot". The hydrodynamic diameter of Au—NP-Pdots was measured with a dynamic light scattering (DLS) spectrometer (Malvern Zetasizer Nano ZS, Worcestershire, United Kingdom). Fluorescence quantum yields were collected using an integrating sphere (model C9920-02, Hamamatsu Photonics) with excitation light from a 150 W CW xenon lamp. The absorption and fluorescence spectra of Au-MC-SC-Pdots were measured with a DU 720 scanning spectrophotometer (Beckman Coulter, Inc., CA) and a Fluorolog-3 fluorospectrometer (HORIBA JobinYvon, NJ), respectively.
5. Dark field and fluorescence microscopy imaging of Au—NP—PFO Pdots. To image Au—NP-Pdots on a coverslip, a drop of the solution containing Au—NP-Pdots was placed on a clear coverslip which was surface modified with (3-aminopropyl)triethoxysilane (APTES). To image Au—NP-Pdots inside cells, the procedure was as follows: When the confluence of HeLa cells in culture flask reached the appropriate level, the cells were harvested from the culture flask by briefly rinsing with culture media followed by incubation with 3 mL of Trypsin-EDTA solution (0.25 w/v Trypsin, 0.53 mM EDTA) at 37° C. for 5 min. After complete detachment, cells were rinsed, centrifuged, and re-suspended in the culture media. One hundred microliters of the suspended cell solution was placed on top of a clean glass coverslip inside a Petri dish. The coverslip was left in cell incubator for 1 h to let the cells attach to the glass surface. Then 1.5 mL of cell culture medium was added to the Petri dish to immerse the coverslip. The Petri dish was left in the cell incubator for 1 day. The proper amount of Au—NP-Pdots solution was next added to the Petri dish, and the cells were incubated for approximately 4 hours. Then the glass coverslip was placed into paraldehyde solution for 15 min to fix the cells before the microscopy experiments were carried out. A Nikon TE2000 inverted microscope was used for imaging. When the microscope was operated in dark-field mode, a numerical aperture (NA) 1.3 oil condenser and a 100× objective with adjustable NA (0.7-1.3) were installed. A 100 W halogen lamp was used as the light source. When the microscope was operated in epi-fluorescence mode, a 405-nm laser was used as the excitation light source and a 410-nm dichroic mirror and 460/80 nm bandpass filter were used to filter the fluorescence emission from the Pdots. Both dark-field and fluorescence images were taken with prosilica cameras (GC1380 and GC660, Newburyport, Mass.).

Figure 4A:
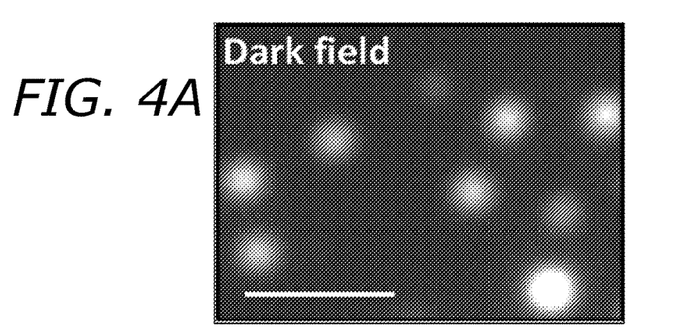
FIGS. 4A-C illustrate dark field and fluorescence microscopy images of Au-MC-SC-Pdots. (A) Dark-field (left) and (B) fluorescence (right) images of Au-MC-SC-Pdots immobilized on a glass coverslip. (C) Dark-field and fluorescence images of Au-MC-SC-Pdots inside cells. (i) Dark-field image of a whole cell; (ii) Magnified image of the red rectangular area in (i); (iii) Corresponding fluorescence image of (ii). The Au-MC-SC-Pdots were the same as those in FIG. 2. Scale bar represents 1 µm.
Figure 4B:
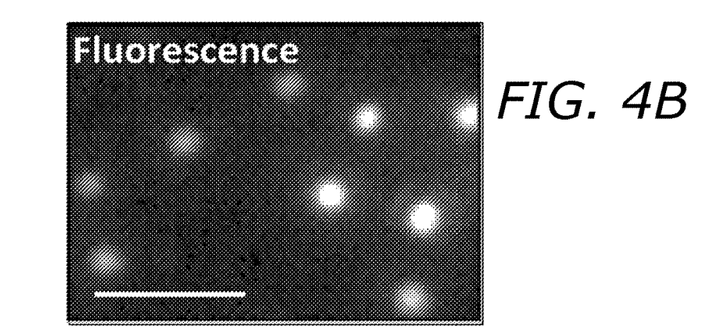
Figure 4C:
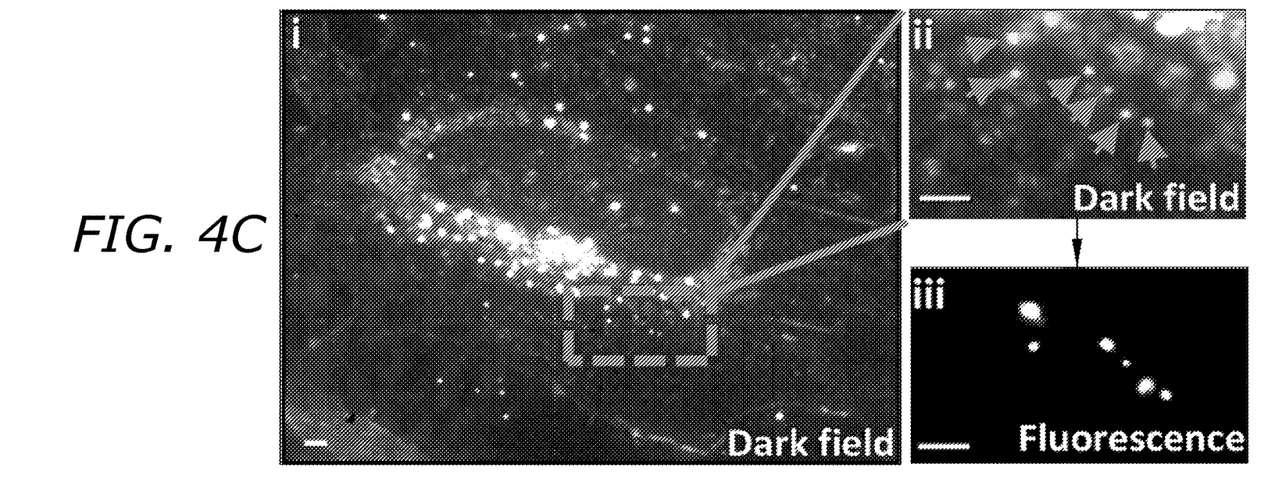

To test whether or not Au—NP-Pdots could serve as dual-modality imaging probes for both dark-field and fluorescence microscopy, they were imaged them using a fluorescence microscope equipped with dark-field optics. Individual Au—NP-Pdots were imaged with excellent signal-to-noise ratio in both dark-field and fluorescence mode (FIG. 4A). The positions of all the Au—NP-Pdots in the two images were correlated. Au—NP-Pdots inside mammalian cells, which represent a more complex environment (FIG.

4B) were also imaged. In dark-field mode, many cellular organelles also strongly scattered light, which made it difficult to differentiate them from Au—NPs. When switched into fluorescence mode, the number of bright spots decreased (FIG. 4B). Each bright spot in fluorescence image had a corresponding bright spot in the dark-field image. Considering that only Au—NP-Pdots can generate both strong fluorescence and scattering signals, we were able to pinpoint the bright spots that appeared in the dark-field image to the six spots (pointed to by arrows) that were from Au—NP-Pdots. Because conjugated polymers do not corrode or damage Au—NPs under the illumination light in normal dark field microscopy, Au—NPs' dark-field scattering photo-stability should not change. Because Au—NPs do not photobleach, they were suitable for long-term particle tracking and imaging in dark-field mode; the fluorescence from the Pdots helped to distinguish these Pdot nanocomposites from other nanoscale cellular features that scattered light.

6. Preparation of $FeO_x$-MC-SC-Pdots. Two milliliters of magnetic NPs in an organic solvent was spun at 14,000 rpm for an appropriate amount of time (1 hour for 10-nm and 20-nm magnetic NPs, 15 minutes for 40-nm magnetic NPs). The pellet was re-dispersed in THF containing PFBT and PS-PEG-COOH under sonication. The solution was subsequently processed in the same way as that for Au—NPs. Pdots containing magnetic NPs were separated from pure Pdots by sucrose gradient centrifugation.

7. Streptavidin conjugation to $FeO_x$-MC-SC-Pdots. In a conjugation reaction, 80 µL of polyethylene glycol (5% w/v PEG, MW 3350) and 80 µL of HEPES buffer (1M, PH 7.3) were added to 4 mL of $Fe_3O_4$-MC-SC-Pdot solution. Streptavidin (1 mg/mL, 30 µL) was then added to the solution and mixed well.

Next, 80 µL of freshly prepared EDC solution (5 mg/mL in MilliQ water) was added to the solution. The above mixture was magnetically stirred for 4 hr at room temperature. The resulting Pdot conjugates were concentrated with a (100K MW) spin column and purified with a Bio-Rad Econo-Pac 10DG column (Hercules, Calif.). After purification, the proper amount of bovine serum albumin (BSA) was added to reach a final concentration of 1% (w/w).

8. Preparation of cell culture for experiments with streptavidin conjugated $FeO_x$-MC-SC-Pdots. The human cervical cancer cell line (HeLa) and breast cancer cell line (MCF-7) were ordered from American Type Culture Collection (ATCC, Manassas, Va., USA). Cells were cultured at 37° C. in 5% $CO_2$ in Eagles Minimum Essential Medium supplemented with 10% fetal bovine serum (FBS) and 1% Pen Strep (5000 units/mL penicillin G, 50 µg/mL streptomycin sulfate in 0.85% NaCl). Cells were pre-cultured prior to experiments until confluence was reached. The cells were harvested from the culture flask by briefly rinsing with culture media, followed by incubation with 3 mL of Trypsin-EDTA solution (0.25% w/v Trypsin, 0.53 mM EDTA) at 37° C. for 5 min. After complete detachment, cells were rinsed, centrifuged, and re-suspended in the culture media. Their concentration was determined by microscopy using a hemacytometer.

9. Cell labeling with $FeO_x$—NP-PFBT Pdots. For labeling a cell-surface marker with IgG conjugates, a million MCF-7 cells in 100-µL labeling buffer (1×PBS, 2 mM EDTA, 1% BSA) were incubated with 0.3 µL of 0.5 mg/mL biotinylated primary anti-human CD326 EpCAM antibody (eBioScience, San Diego, Calif.) on a rotary shaker in the dark and at room temperature for 30 minutes, followed by a washing step using labeling buffer. Then the cells were incubated with streptavidin-conjugated Pdots in BlockAid™ blocking buffer (Invitrogen, Eugene, Oreg.) for 30 minutes on a shaker in the dark and at room temperature, followed by two washing steps with labeling buffer. Cells were later fixed by dissolving the cell pellet obtained by centrifugation in 500 µL of fixing buffer (1×PBS, 2 mM EDTA, 1% BSA, 1% paraformaldehyde).

10. Imaging cells labeled with $FeO_x$—NP-PFBT Pdots. A Nikon TE2000 inverted microscope was used for imaging. When the microscope was operated in differential interference contrast (DIC) mode, a numerical aperture (NA) 1.3 oil condenser, a 100× objective with NA 1.4, two polarizers and Nomarski prisms were installed. A 100 W halogen lamp was used as the light source. When the microscope was operated in epi-fluorescence mode, a 488-nm laser was used as the excitation light source, and a 505-nm dichroic mirror and 550/60 nm bandpass filter were used to filter the fluorescence emission from the Pdots. Both DIC and fluorescence images were taken with prosilica cameras (GC1380 and GC660, Newburyport, Mass.).

Figure 5A:
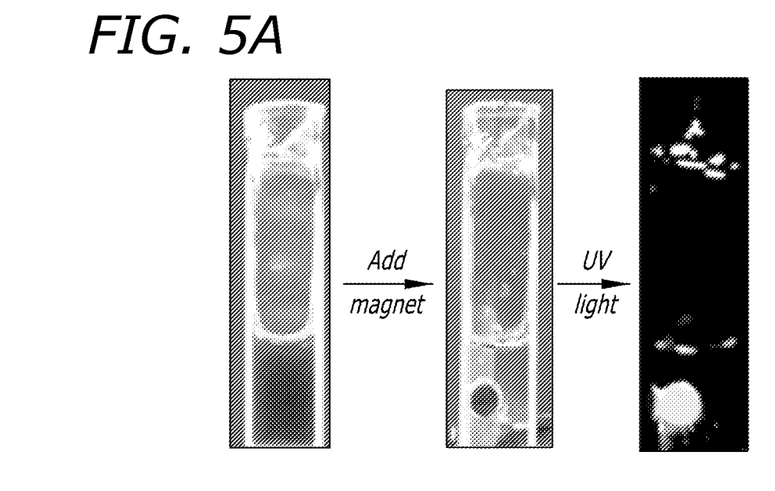
FIGS. 5A-C illustrate immuno-magnetic isolation of cells labeled with $FeO_x$-MC-SC-Pdots. (A) Manipulation of $FeO_x$-MC-SC-Pdots dispersed in aqueous solution with a permanent magnet. (B) Schematic showing the bioconjugation of $FeO_x$-MC-SC-Pdots to streptavidin for labeling the cell-surface protein, EpCAM. (C) Immuno-magnetic separation of cells labeled with $FeO_x$-MC-SC-Pdots with a permanent magnet. Images to the right show an isolated cell. Scale bar represents 5 µm.
Figure 5B:
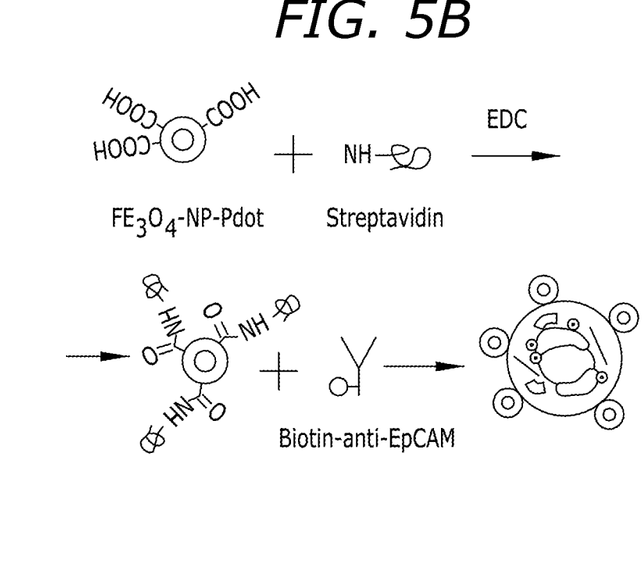
Figure 5C:
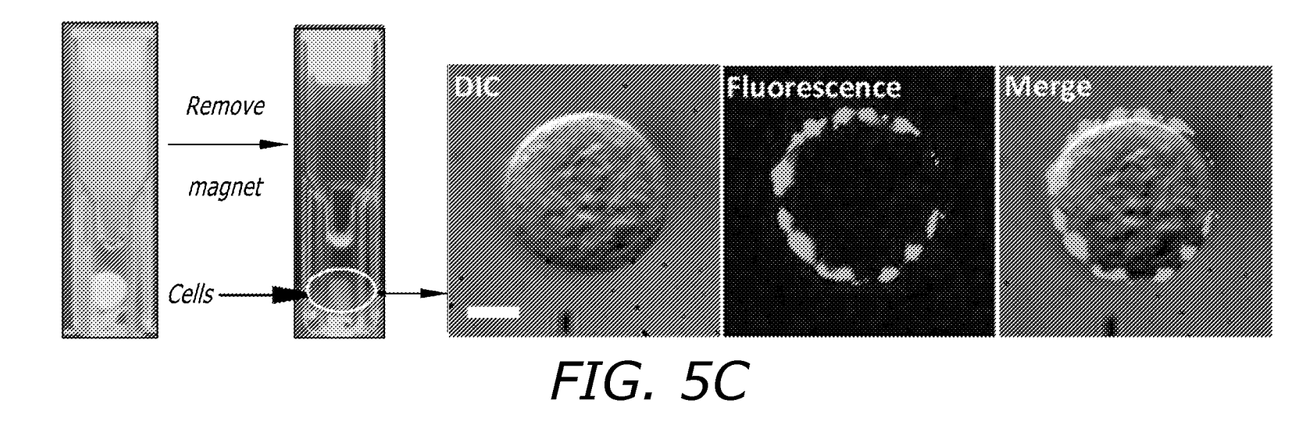
Figure 6A:
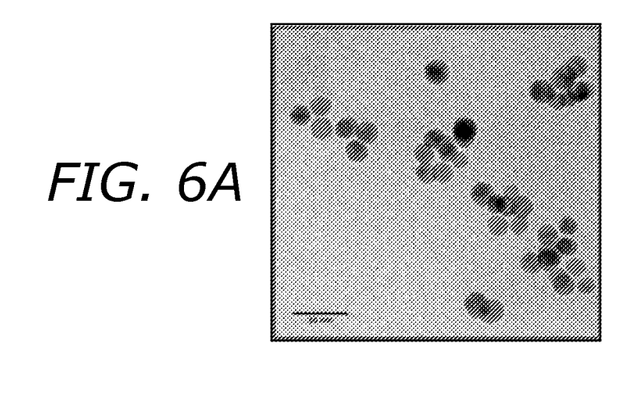
FIGS. 6A-B illustrate characteristics of synthesized Au-MC-SC-Pdots. (A) TEM image of Au-MC-SC-Pdots. (B) Size histogram of Au-MC-SC-Pdots. The average size was 6.5 nm. Scale bar represents 20 nm.
Figure 6B:
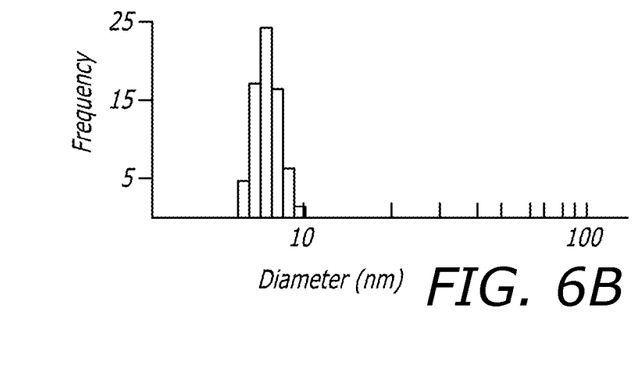
Figure 7A:
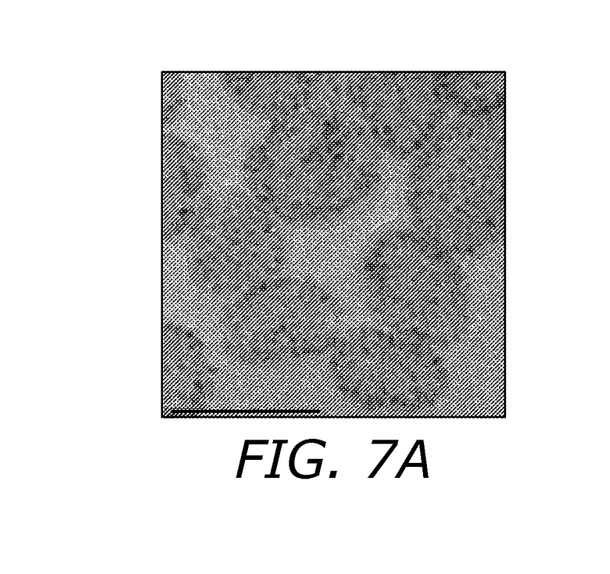
FIGS. 7A-B illustrate TEM images of magnetic NPs embedded PFO-Pdots (FeO$_x$-MC-SC-Pdots). A) FeO$_x$-MC-SC-Pdots containing 10 nm magnetic NPs. B) FeO$_x$-MC-SC-Pdots containing 20 nm magnetic NPs. Scale bar represents 100 nm.
Figure 7B:
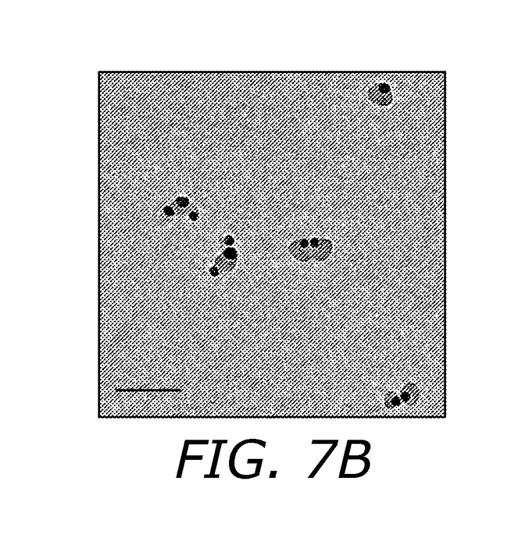

11. MC-SC-Pdots and Magnetism. For $FeO_x$-MC-SC-Pdots, their potential application in both bioimaging and sample preparation was tested. $FeO_x$-MC-SC-Pdots containing magnetic NPs of various sizes (10 nm, 20 nm and 40 nm) (see FIG. 7) were successfully prepared. These $FeO_x$-MC-SC-Pdots were attracted to and concentrated by a magnet; the hybrid $FeO_x$-MC-SC-Pdots emitted strong fluorescence when excited by UV light (FIG. 5A). During $FeO_x$-MC-SC-Pdot preparation, the high molecular weight polymer PS-PEG-COOH was blended into the hybrid Pdots. The carboxylic acid groups on the FeOx-MC-SC-Pdot's surface enabled facile bioconjugation with streptavidin through a simple EDC reaction (FIG. 5B). The MCF-7 cancer cell line was then labeled with streptavidin-conjugated $FeO_x$-MC-SC-Pdots and a biotinylated primary antibody against EpCAM, a cell-surface protein commonly used to isolate circulating tumor cells. The $FeO_x$-MC-SC-Pdot-labeled cells could be manipulated and enriched using a permanent magnet (FIG. 5C). In FIG. 5C, it can be seen that the majority of labeled cells were successfully attracted to the magnet. Given that stronger magnet and magnetic NPs can be used, the cell separation efficiency may be further improved if necessary. To further confirm that cells concentrated by the magnet had $FeO_x$-MC-SC-Pdots, the isolated cells were imaged by fluorescence microscopy, which confirmed the presence of $FeO_x$-MC-SC-Pdots on the cell surface (FIG. 5C). In this way, $FeO_x$-MC-SC-Pdots can be used for cell enrichment and isolation, similar to the use of $FeO_x$—NPs for immuno-magnetic isolation, as well as for cellular imaging and detection by taking advantage of the strong fluorescence signal from Pdots.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would negate the MC-SC-Pdot's functional use in cellular imaging or manipulation or, in processes of production would produce MC-SC-Pdot significantly less suitable for use in cellular imaging or manipulation. As used herein, "significantly less suitable" means a statistically significant difference in a measurable quality of the Pdot's performance in cellular imaging or manipulation.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, $3^{rd}$ Edition or a dictionary known to those of skill in the art, such as the Oxford Dictionary of Biochemistry and Molecular Biology (Ed. Anthony Smith, Oxford University Press, Oxford, 2004).

What is claimed is:

1. A metal-containing (MC) semiconducting (SC) polymer dot (Pdot) comprising:
   (i) a hydrophobic core comprising a hydrophobic polymer attached to a single metal nanoparticle (NP), the single metal NP comprising a metal, wherein the metal comprises Au, Ni, Co, Ga, Fe, an oxide thereof, a complex thereof, an alloy thereof, or a combination thereof; and
   (ii) a fluorescent SC polymer surrounding and outside of the hydrophobic core.

2. The MC-SC-Pdot of claim 1, wherein the single metal nanoparticle comprises Au or Fe.

3. The MC-SC-Pdot of claim 2, wherein the single metal nanoparticle comprises an iron oxide.

4. A composition comprising a plurality of the MC-SC-Pdots of claim 1, wherein the plurality of the MC-SC-Pdots has an average diameter of less than about 80 nm.

5. The MC-SC-Pdot of claim 1, wherein the SC polymer forms at least about 80% v/v of the MC-SC-Pdot.

6. The MC-SC-Pdot of claim 1, having an absorption wavelength between about 350 nm and about 850 nm.

7. The MC-SC-Pdot of claim 1, wherein the hydrophobic polymer is selected from the group consisting of poly(meth)acrylate, polyacrylamide, polyisobutylene, polydiene, polyphenylene, polyethylene, polylactide, polystyrene, polysiloxane, poly(vinylpyrrolidone), polyurethane, a block copolymer thereof, a random or alternating copolymer thereof.

8. The MC-SC-Pdot of claim 1, wherein the SC polymer is selected from the group consisting of Poly(9,9-dihexylfluorenyl-2,7-diyl) (PDHF); Poly(9,9-dioctylfluorenyl-2,7-diyl) (PFO), Poly[{9,9-dioctyl-2,7-divinylene-fluorenylene}-alt-co-{2-methoxy-5-(2-ethylhexyloxy)-1,4-phenylene}] (PFPV); Poly[(9,9-dioctylfluorenyl-2,7-diyl)-co-(1,4-benzo-{2,1,3}-thiadiazole)] (PFBT); Poly[(9,9-dioctylfluorenyl-2,7-diyl)-co-(4,7-Di-2-thienyl-2,1,3-benzothiadiazole)] (PFTBT); Poly[(9,9-dioctylfluorenyl-2,7-diyl)$_{0.9}$-co-(4,7-Di-2-thienyl-2,1,3-benzothiadiazole)$_{0.1}$] (PF-0.1T-BT), Poly[2-methoxy-5-(2-ethylhexyloxy)-1,4-phenylenevinylene] (MEH-PPV); Poly(2,5-di(3',7'-dimethyloctyl)phenylene-1,4-ethynylene) (PPE), [(BODIPY)$_{0.02}$-fluorene], Poly[(BODIPY)$_{0.05}$-fluorene], Poly[(BODIPY)$_{0.10}$-fluorene], Poly[(BODIPY)$_{0.25}$-fluorene], and Poly[(BODIPY)$_{0.50}$-fluorene].

9. The MC-SC-Pdot of claim 1, wherein the hydrophobic polymer comprises carboxylic acid terminated polystyrene-poly(ethylene glycol) polymers.

10. The MC-SC-Pdot of claim 1, wherein the SC polymer is selected from PFO, PFBT, and combinations thereof.

11. The MC-SC Pot of claim 1, wherein the SC polymer is a copolymer comprising at least two different SC units, and wherein the at least two different SC units are selected from the group consisting of fluorene units, phenylene vinylene units, phenylene units, phenylene ethynylene units, benzothiazole units, thiophene units, carbazole fluorene units, boron-dipyrromethene units, and derivatives thereof.

* * * * *

UNITED STATES PATENT AND TRADEMARK OFFICE
CERTIFICATE OF CORRECTION

| | | |
|---|---|---|
| PATENT NO. | : 11,249,073 B2 | Page 1 of 1 |
| APPLICATION NO. | : 14/434200 | |
| DATED | : February 15, 2022 | |
| INVENTOR(S) | : D. Chiu et al. | |

It is certified that error appears in the above-identified patent and that said Letters Patent is hereby corrected as shown below:

In the Claims

| Column | Line | |
|---|---|---|
| 18 | 17 | Claim 11, change "MC-SC Pot" to -- MC-SC-Pdot -- |

Signed and Sealed this
Twenty-first Day of February, 2023

*Katherine Kelly Vidal*

Katherine Kelly Vidal
*Director of the United States Patent and Trademark Office*